United States Patent [19]

Hesselgren

[11] 4,406,708

[45] Sep. 27, 1983

[54] METHODS FOR UTILIZING DENTAL PROSTHESES

[76] Inventor: Sven-Gunnar Hesselgren, Kummelvagen 19, S-161 39 Bromma, Sweden

[21] Appl. No.: 353,802

[22] Filed: Mar. 1, 1982

Related U.S. Application Data

[63] Continuation-in-part of Ser. No. 47,050, Jun. 11, 1979, Pat. No. 4,339,279.

[30] Foreign Application Priority Data

Jun. 16, 1978 [SE] Sweden ............................... 7806939

[51] Int. Cl.$^3$ ........................... A61K 5/00; C08L 1/26; B08B 7/04
[52] U.S. Cl. ............................ 134/37; 106/35; 106/194; 106/15.05; 252/106; 424/44; 428/532
[58] Field of Search ............... 106/35, 194, 197 C; 252/100, 136, 106; 433/216; 428/532; 134/2, 41, 37; 424/44

[56] References Cited

U.S. PATENT DOCUMENTS

| | | | |
|---|---|---|---|
| 2,701,212 | 2/1955 | Brennan | 106/35 |
| 3,868,260 | 2/1975 | Keegan et al. | 106/35 |
| 3,962,107 | 6/1976 | Levin et al. | 252/100 |
| 3,997,459 | 12/1976 | Bogie et al. | 142/100 |
| 4,339,279 | 7/1982 | Hesselgren | 106/194 |

OTHER PUBLICATIONS

"Uses and Applications of Chemicals and Related Materials", Gregory, T. C., Jun. 44, pp. 526 and 527.

*Primary Examiner*—Theodore Morris
*Attorney, Agent, or Firm*—Lerner, David, Littenberg, Krumholz & Mentlik

[57] ABSTRACT

Methods for utilizing a dental prosthesis are disclosed. In particular, the methods for utilizing a dental prosthesis include applying a retention composition including an effective amount of an orally acceptable retention agent so as to provide sufficient adhesive characteristics to the composition to maintain the prosthesis in position in the mouth of a subject, and an effective amount of sodium bicarbonate to inhibit the growth of bacteria and fungi. Methods for utilizing and/or cleaning dental prosthesis are also disclosed, including employing these retention compositions to retain the dental prosthesis against the oral mucous membrane, and then contacting the dental prosthesis containing the retention composition after use with an acidic medium so that the sodium bicarbonate and the acidic medium react to generate gas bubbles which effectively burst the retention composition adhering to the prosthesis.

14 Claims, No Drawings

METHODS FOR UTILIZING DENTAL PROSTHESES

This application is a continuation-in-part of application Ser. No. 47,050 filed June 11, 1979, now U.S. Pat. No. 4,339,279.

FIELD OF THE INVENTION

The present invention relates to methods for utilizing dental prostheses. More particularly, the present invention relates to methods for utilizing and/or removing used retention composition from such dental prostheses. Still more particularly, the present invention relates to methods for utilizing and/or removing from dental prostheses used retention compositions which have been used to retain the prosthesis in position against the oral mucous membrane.

BACKGROUND OF THE INVENTION

The effective removal of adhesive retention agents during the cleaning of dental prostheses that can be taken out of the mouth is of essential importance in avoiding inflammatory changes in the mucous membrane, which in turn result from the concentrated growth of bacteria and fungi in any remaining retention agent.

Many wearers (about 50-65%) of removable dental prostheses have varying degrees of difficulty with their prosthesis. (See Miller E. L., 1975, J. Dent. Assn. S. AFR. 30 (1): 89-93 and Budtz-Jorgensen E., 1978, JADA, 96, 96: 474-479). These troubles may manifest themselves in different ways, and their causes are varied.

Maintaining the prosthesis fixed in its intended position both during rest or relaxation and while speaking, and most importantly during the movements connected with chewing, may also be a problem for many people.

These inconveniences may still appear even where the prosthesis has been constructed in accordance with all of the rules pertaining to dental artistry. The reason for this may be the presence of unalterable and unfavorable anatomic oral conditions, or other individual causes, such as motoric insufficiencies in the oral region, such as near the jaw. These insufficiencies often occur with certain categories of people, such as old people and physically or mentally handicapped people. (See Norderram E., 1977: Vol. 69, No. 7). The inability to fix the prosthesis causes a feeling of insecurity in the individual, and is often a psychological handicap during social contact with other people.

It is also not unusual among denture wearers for inflammatory changes to occur in the oral mucous membrane against which the base of the prosthesis abuts. Through intensified research in this field, it has now been established that the primary cause of such disease conditions are of microbial nature, with the emphasis on the occurrence of fungi. The inflammatory conditions in the mucous membrane are thus often related to the occurrence of fungi in the base of the prosthesis itself, which is extremely difficult to overcome. (See Budtz-Jorgensen E., 1974: Scan. J. Dent. Res. 82:151).

There have been various practical solutions which have therefore been previously attempted so as to eliminate these problems. Thus, in order to improve the retention of the prosthesis, it is extremely common to apply a fixing preparation containing an adhesive or glue-like material, preferably sodium carboxy methyl cellulose, onto the surface of the prosthesis facing the oral mucous membrane, normally termed the mucous membrane surface of the prosthesis. These fixing preparations usually consist of a powder, which is applied onto the mucous membrane surface of the prosthesis, and which comes into contact with the saliva-coated or saliva-producing mucous membrane, thereby forming a gel with adhesive action. On the other hand, the prosthesis is sometimes moistened with some water before insertion into the mouth, and also in order to improve the gel formation. Fixing preparations are also available in the form of a paste, which is manufactured in a ready-to-use form. The gelling or adhesive agent of such fixing preparations is generally sodium carboxy methyl cellulose.

The method thus described enables the wearer to improve the fixing of the prosthesis in a simple manner. For this reason, it is often used. However, it has certain drawbacks, particularly if the composition is applied over long periods of time. These fixing preparations do not inhibit the bacteria and fungus flora which normally exist and in the oral cavity. To the contrary, experience has shown that they may promote the chance of colonization for these micro-organisms. Therefore, chemical inhibitors have been added to some types of fixing agents in order to prevent such growth, but these have, in turn, resulted in new problems. That is, the continued use of such chemical inhibitors may readily produce toxic and allergic reactions in the mucous membrane tissues as a result of inhibitor exposure, particularly when such use is extended over a number of years of intermittent application.

Irrespective of whether the denture wearer uses a retention composition or not, he must always carry out a careful program of oral hygiene including the daily cleansing of the prosthesis, mouth and any remaining teeth, in order to remove bacteria plaque which is continuously being produced, as well as the collection of food particles, the occurrence of which is difficult to prevent. (See Hedegard E., 1977: Vol. 69, No. 7). Apart from the more unpleasant feeling of bad odour and taste, the insufficient prosthetic and oral hygiene may give rise to a state of inflammation, or even serious alterations in the mucous membrane, known as prosthesis stomatites, and to caries attacks on the remaining teeth.

It is very difficult to remove these adhesive gels, and this therefore must be done by an active mechanical method, such as by scraping, brushing, and at the same time rinsing. In spite of this, some adhesive gel often remains, and it is very hard to detect since the gel is transparent.

In order to clean the prosthesis as efficiently and gently as possible, dentists recommend brushing with a soft brush and suitable chemical wetting agent, preferably having microbicidal properties (See Andrup B., 1977: Swed. Dent. J., Vol. 66:181).

Due to inconvenience and difficulty in removing these adhesive gels, many patients and nurses fail to execute this cleaning operation effectively, and therefore the result is a heavy remaining bacteria and fungi effection.

In connection with chemical cleansing, there are a number of compositions available which are especially intended for use with such prostheses. Basically, these cleansing compositions consist of a combination of two or more chemical substances in powder or tablet form which, when dissolved in water, vigorously react with each other, producing gas or bubbles ($CO_2$). It is this effervescing solution which is thus intended to automatically remove the coating of bacteria plaque and remnants of fixing agent from the prosthesis when it is immersed therein, and if successful, this can be done without further mechanical cleansing.

However, there are certain disadvantages associated with this course of action. For example, this is just a one-way action in which the bubbles mechanically wear away the tacky retention agent, which is normally very hard to remove completely. Moreover, this type of cleaning agent becomes very expensive for the users.

SUMMARY OF THE INVENTION

It is therefore an object of the present invention to eliminate the disadvantages associated with the previously known retention agents, and in these contained substances inhibiting growth of fungi and bacteria, and also to provide a simple and effective method to clean dental prosthesis from used, tacky retention agents or adhesives.

In accordance with the present invention, this and other objects have now been attained by the discovery of the method of this invention in which a dental prosthesis is utilized, including applying to that prosthesis a retention agent including an effective amount of an orally acceptable retention agent so as to provide sufficient adhesive characteristics to that composition to maintain the dental prosthesis in position in the mouth of a subject, and an effective amount of sodium bicarbonate to inhibit the growth of bacteria and fungi.

In accordance with another embodiment of the method of the present invention, a dental prosthesis is utilized by employing a retention composition to retain the dental prosthesis against the oral mucous membrane, and in which the retention composition similarly comprises a retention composition including an effective amount of an orally acceptable retention agent so as to provide sufficient adhesive characteristics to the composition to maintain the prosthesis in position in the mouth, and an effective amount of sodium bicarbonate to inhibit the growth of bacteria and fungi, and contacting the dental prosthesis containing the retention composition after use with an acidic medium so that the sodium bicarbonate and the acidic medium can react in order to generate gas bubbles which are effective to burst the retention composition adhering to the dental prosthesis.

In accordance with a preferred embodiment of the method of the present invention, the sodium bicarbonate is included in a retention composition in amounts of up to about 75% by weight, calculated on the weight of the retention composition, and preferably between about 25 and 75% by weight thereof. Preferably, after use the dental prosthesis is brought into contact with an acidic medium in the form of an aqueous solution, and this can be accomplished by methods such as contacting the dental prosthesis with a serviette or cloth soaked with the acidic medium, or by placing the dental prosthesis in a container which includes that acidic medium. In a preferred embodiment, the acidic medium is a weak acid which will not be harmful to the user, such as acetic acid, citric acid, tartaric acid, etc.

By employing the methods of the present invention, firstly the entire risk of toxic or allergic action on the mucous membranes, which have been caused by the chemical fungus and bacteria inhibitors previously used, can now be eliminated. This is now possible because the compound preventing the growth of bacteria and fungi essentially consists of sodium bicarbonate. On the basis of microbiological experiments, it has thus been found that in its water-soluble state, sodium bicarbonate is an efficient inhibitor for the growth of bacteria, and particularly for the growth of fungi, which is so difficult to overcome. Without being limited to any theory, it is believed that it is principally the high pH value which causes this inhibition of growth. That is, the growth of fungus is primarily encouraged in acid surroundings. The sodium bicarbonate can thus replace the previously used bacteria inhibitors, which were in some respects harmful.

A further advantage which can be realized in accordance with this invention is that one of the components in that acid-base pair which is used is already contained in the retention composition. The effect of this is that the acid can be said to peel off the adhesive from the outside, and by securing acid in excess all of the adhesive or retention composition can be removed from all surface of the dental prosthesis.

DETAILED DESCRIPTION

It is unavoidable that small amounts of either the retention composition utilized, or one or more of its constituents will become dissolved in the saliva in the oral cavity. However, it is not dangerous to swallow the sodium bicarbonate component in the amounts occurring here. In fact, it is generally known that sodium bicarbonate is widely used for treating ordinary stomach troubles in considerably larger doses, and without evidence of any negative side effects.

The appearance of inflammatory changes in the oral mucous membrane, which is primarily caused by the presence of fungi on the mucous membrane side of the prosthesis, is thus surprisingly counteracted by the methods of the present invention employing a retention composition containing sodium bicarbonate which, among other things, acts as an inhibitor for the growth of bacteria and fungi. The problems arising from the use of the previously known chemical inhibitors described above are at the same time eliminated, since the risk of toxic and allergic action on the mucous membrances is removed. Furthermore, these retention compositions, according to the invention, can be used without interruption over a long period of time, and need not be replaced by such a composition which need be free from chemical inhibitors. An additional advantage is realized by use of the sodium bicarbonate component in the retention compositions hereof. Thus, it is also known that the remaining original teeth are extremely prone to caries attacks in the case of the combined use of partial prosthesis. Since the caries process is characterized by an acid attack on the hard tissues of the teeth, where the sodium bicarbonate is released by the saliva, or where the retention agent is in direct contact with the dental surfaces, it serves as a buffer against a lowering of the pH value, and thus contributes to preventing such caries.

As discussed above, the retention compositions used in the method of this invention contain a retention agent which produces the requisite properties for the desired retention when the composition is applied. This agent and/or special, inert additives included therein, also acts as a carrier for the sodium bicarbonate, and thus as a depot for the sodium carbonate, from which a saturated solution is continuously released. The retention agent can be generally defined as a fixing agent, whereby fixation is meant adhesive securing. Such a retention agent is sodium carboxy methyl cellulose which, in contact with an aqueous liquid or saliva, has a sticky consistency, with adhesive or glue-like properties. Other alkali metal salts of carboxy methyl cellulose can also be used. As mentioned above, sodium carboxy methyl cellulose is a known retention agent in such compositions. Other known retention agents can also be used, such as acacia (rubber), dextrine and starch. Additives such as polyether and polyacrylates may also be included in the composition in order to reduce the solubility of the retention agent in water, and to control the consistency of the composition.

Microbiological experiments have been performed to determine the degree of growth inhibition, and these experiments are described in the following examples.

EXAMPLE 1

A saturated solution of sodium bicarbonate (8 grams) was added to a number of test tubes containing 10 ml of broth for bacteria cultivation (nutrient broth, Difco). Thereafter, one drop of a pure culture of fungus (Candida Albicans), which was 24-hours old, was innoculated in each test tube. Cultivation was then carried out at 37° C., for three days. In no case could any growth be established. However, a corresponding number of control experiments performed without the addition of sodium bicarbonate all showed growth.

EXAMPLE 2

Similar experiments to those described in Example 1 above were also performed with innoculation of fresh saliva. The results were in agreement with those obtained in the above experiments with fungus, i.e. no growth was noted.

The use of a retention composition containing sodium bicarbonate results in the important additional improvement that sodium bicarbonate remaining on the dental prosthesis acts as a subsequent reaction agent when it is reacted with an acid or an acidified cleaning agent dissolved in water, for instance. This means that the cleaning composition can be made cheaper than conventional compositions, since it is unnecessary to have any latent reaction agent for the acid in the cleaning composition.

The cleaning liquid may consist only of an acid, such as acetic acid, for use in the household, or can be prepared by dissolving in water a suitable amount of a cleaning composition containing as its main component an acid, such as citric acid, along with suitable detergents. When the prosthesis is then immersed in this acid solution, a chemical reaction with strong foaming will then occur between the remaining deposits of sodium bicarbonate on the prosthesis base and the acid in the water solution. The retention mass is thus gradually loosened from the surface of the prosthesis as long as there is an excess of acid. It will be understood that the proportions of alkali and acid can be easily adjusted so that the entire content of sodium bicarbonate in the retention mass is consumed. The prosthesis is thus completely freed from the sticky coating in which the sodium bicarbonate is incorporated.

The reaction which occurs is intense, and it gives rise to the formation of carbon dioxide. This reaction takes place inside the retention gel, and the gas thus formed will blow up or burst the adhesive gel, which will then be loosened from the surface of the prosthesis. Removal of the adhesive gel, and thus cleaning of the prosthesis, can therefore be achieved without the need for any mechanical brushing.

An excess of acid in the cleaning bath will also very carefully dissolve tartar, which has precipitated on the prosthesis and which is very hard to remove mechanically.

The effects of such adhesive removal has been verified by simple model tests, described in the following example.

EXAMPLE 3

The same amount of adhesive gel made from different powder compositions was applied to covering glasses (for a microscope).

These covering glasses were then immersed in an acid dissolved in water. Citric acid, tartaric acid or acetic acid could be utilized.

After a predetermined time period, which varied between 5 and 30 minutes in different tests, the covering glasses were visually inspected, and the remaining amounts of gel on the different covering glasses were compared relative to each other. To simplify the registration, an inert coloring agent was added to the adhesive gels. In this case, methylene blue was utilized.

The different powder compositions employed comprised:

A. 100% by weight carboxy methyl cellulose (CMC)
B. 75 by weight carboxy + 25% by weight sodium bicarbonate
C. 50 by weight carboxy + 50 by weight sodium bicarbonate
D. 25 by weight carboxy + 75 by weight sodium bicarbonate Gels manufactured from compositions B, C and D were removed with much more ease than was composition A, without any added sodium bicarbonate. Comparing compositions B, C and D relative to each other, it can be seen that the gel was easier to remove with increasing amount of sodium bicarbonate.

In adhesion tests, it has also been shown that compositions containing the same amounts by weight of CMC and sodium bicarbonate give the same adhesive effect as compositions containing only CMC. This percentage formula has therefore been used in clinical applications.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What is claimed is:

1. A method for utilizing a dental prosthesis comprising applying to said dental prosthesis a retention composition comprising (1) an effective amount of an orally acceptable retention agent to provide sufficient adhesive characteristics to said composition to maintain said dental prosthesis in position in the mouth of a subject; and (2) an effective amount of sodium bicarbonate to inhibit the growth of bacteria and fungi.

2. The method of claim 1 wherein said sodium bicarbonate is present in an amount of less than about 75% by weight of said composition.

3. The method of claim 2 wherein said sodium bicarbonate is present in an amount of between about 25 and 75% by weight of said composition.

4. The method of claim 1 wherein said orally acceptable retention agent is selected from a group consisting of an alkali metal salt of carboxymethyl cellulose, acacia, dextrine, starch, and mixtures thereof.

5. The method of claim 4 wherein said orally acceptable retention agent comprises an alkali metal salt of carboxymethyl cellulose.

6. The method of claim 5 wherein said orally acceptable retention agent comprises a sodium salt of carboxymethyl cellulose.

7. A method for utilizing a dental prosthesis comprising employing a retention composition to retain said dental prosthesis against the oral mucuous membrane, said retention composition comprising an effective amount of an orally acceptable retention agent to provide sufficient adhesive characteristics to said composition to maintain said dental prosthesis in position in the mouth, and an effective amount of sodium bicarbonate to inhibit the growth of bacteria and fungi, and contacting said dental prosthesis containing said retention composition after use with an acidic medium whereby said sodium bicarbonate and said acidic medium may react so as to generate gas bubbles which are effective to burst said retention composition adhering to said dental prosthesis.

8. The method of claim 7 wherein said sodium bicarbonate is present in an amount of less than about 75% by weight of said composition.

9. The method of claim 7 wherein said sodium bicarbonate is present in an amount of between about 25 and 35% by weight of said composition.

10. The method of claim 7 wherein said acidic medium is in the form of an aqueous solution.

11. The method of claim 7 wherein said contacting of said dental prosthesis with said acidic medium comprises placing said dental prosthesis in a container including said acidic medium therein.

12. The method of claim 7 wherein said contacting of said dental prosthesis with said acidic medium comprises contacting said dental prosthesis with a serviette or cloth soaked with said acidic medium.

13. The method of claim 7 wherein said acidic medium comprises a weak acid.

14. The method of claim 13 wherein said weak acid is selected from the group consisting of acidic acid, citric acid, tartaric acid, and mixtures thereof.

* * * * *